United States Patent [19]

Carpenter

[11] Patent Number: 5,587,539
[45] Date of Patent: Dec. 24, 1996

[54] GRAB SAMPLER

[76] Inventor: John K. Carpenter, 12148 Dunsinane, Bridgeton, Mo. 63044

[21] Appl. No.: 259,391

[22] Filed: Jun. 14, 1994

[51] Int. Cl.⁶ .................................................. G01N 1/20
[52] U.S. Cl. ................................................... 73/863.52
[58] Field of Search .......................... 73/863.41, 863.42, 73/863.45, 863.51–863.58, 864.31, 864.33, 864.51, 864.63, 864.73, 863.52

[56] References Cited

U.S. PATENT DOCUMENTS

| | | |
|---|---|---|
| 491,676 | 5/1978 | Niskin . |
| 2,388,548 | 11/1945 | Jurs . |
| 2,675,706 | 4/1954 | Edgar . |
| 2,958,222 | 11/1960 | Morgan ............................ 73/864.31 |
| 3,924,471 | 12/1975 | Singer . |
| 4,037,477 | 7/1977 | Niskin . |
| 4,089,209 | 5/1978 | Grana . |
| 4,317,378 | 3/1982 | Mustard ............................. 73/863.52 |
| 4,574,645 | 3/1986 | Allen et al. ........................ 73/863.51 |
| 4,583,293 | 4/1986 | Smith . |
| 4,625,571 | 12/1986 | Slater . |
| 4,864,877 | 9/1989 | Ortiz . |
| 4,958,528 | 9/1990 | Garrison . |

OTHER PUBLICATIONS

Survey of Commercially Available Automatic Wastewater Samplers, EPA 600/4–76–051 Sep. 1976 Richard P. Lauch.
Wastewater Samplers ISCO Brochure No. 1392 Dec. 1974.
Wastewater Samplers and Recording Flow Meters ISCO Brochure No. 1392–04 Dec. 1975.

*Primary Examiner*—Robert Raevis
*Attorney, Agent, or Firm*—Dennis A. Bennett

[57] ABSTRACT

There is disclosed a novel sampling device. This invention is capable of taking a grab sample when a predetermined level of discharge like water has occurred. It is designed to be easily moved and set up.

20 Claims, 5 Drawing Sheets

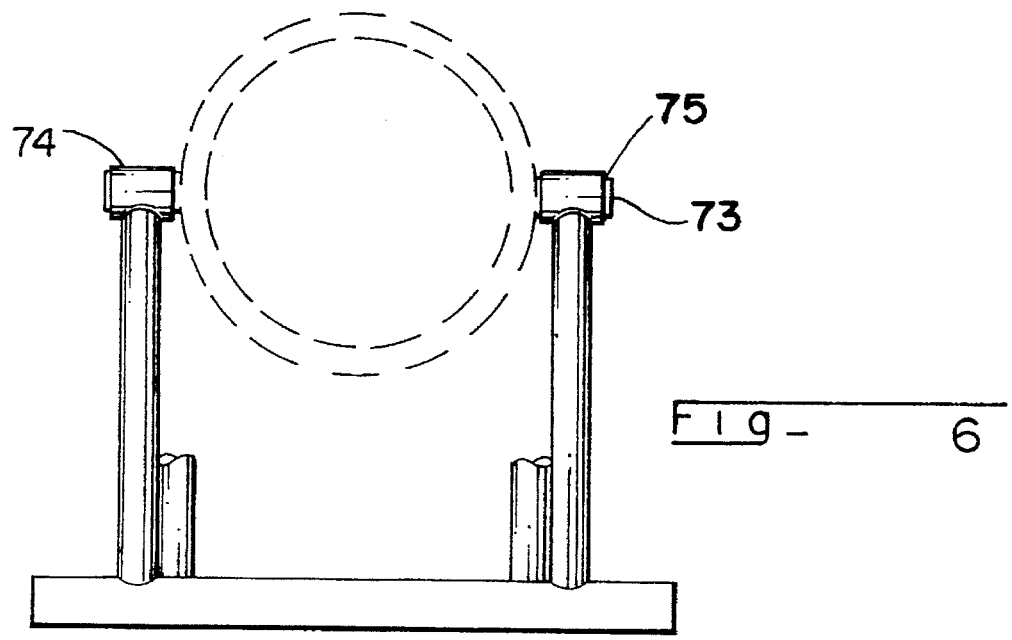
Fig - 6
Fig - 7
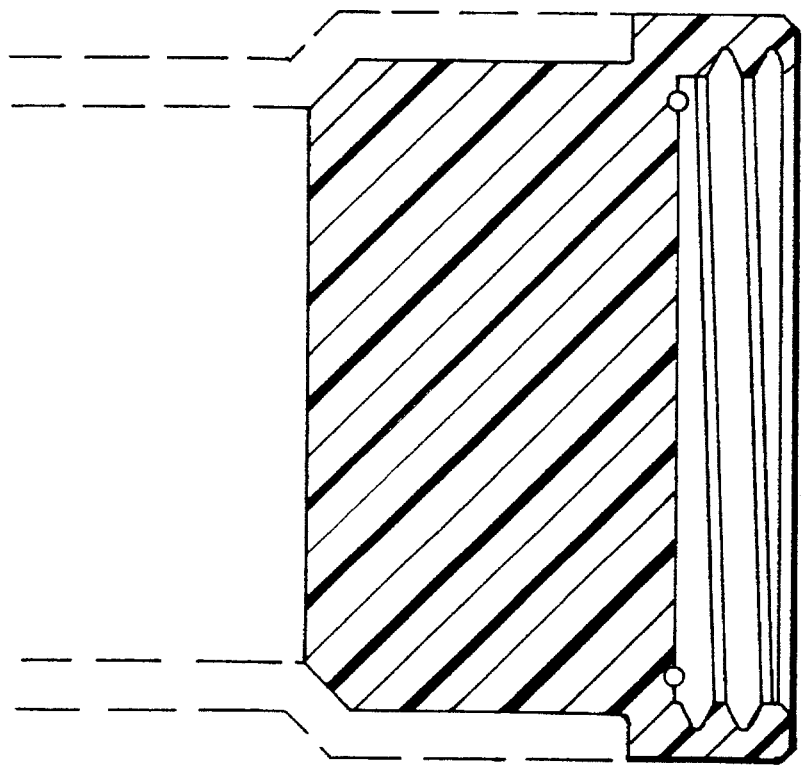

GRAB SAMPLER

FIELD OF THE INVENTION

The present invention relates to a sampling device and more particularly, this invention relates to an inexpensive grab sampler used in collecting samples of runoff water.

BACKGROUND OF THE INVENTION

Over the past decade, more stringent laws and regulations have been imposed on companies' discharge of various industrial waste by-products into the waters, lakes and streams. Companies' document pollutant levels in their area to verify that they are complying with these requirements.

The pollutant level in municipal and industrial storm water discharge is a useful parameter in determining a plurality of different pollutant levels. First of all, this can determine the pollutant level in the air, as some of the pollutant level in the air will become dissolved in the rainwater that falls. In addition, there is a certain amount of silt which will also be collected. This silt will be somewhat representative of the pollutant level in and running off from the soil. Oil, grease, and leach ate from stored or spilled chemicals or raw materials can also be found in storm water discharge.

Accordingly, the EPA has issued rules that require that samples be collected from the discharge resulting from a storm event that is greater than 0.1 inches in magnitude and that occurs at least 72 hours from the. previously measurable (greater than 0.1 inch rainfall) storm event. The EPA requires a grab sample shall be taken during the first thirty minutes of the discharge. If the collection of a grab sample during the first thirty minutes is impracticable, a grab sample can be taken during the first hour of the discharge, but then discharge must submit with the monitoring report a description of why a grab sample during the first thirty minutes was impracticable.

In order to comply with these regulations, a grab sampling device is needed that is inexpensive, reliable and is able to be calibrated to take a sample only when a certain level of discharge is present.

There have been many devices proposed to comply with the regulation. A runoff water trap is disclosed in U.S. Pat. No. 4,958,528 to Garrison. It uses a float valve to control when a sample is taken.

U.S. Pat. No. 1,742,400 to Larsson defines a structure which uses a float to open and close a valve. U.S. Pat. No. 2,388,548 to Jurs uses a complicated sequence of weights, pulleys and arms in order to open and close a valve.

BRIEF DESCRIPTION OF THE DRAWINGS

FIG. 6 is a front view of the top portion of the pivot support means.

FIG. 7 is a cut way side view of a low cost thread adapter.

SUMMARY OF THE INVENTION

There is disclosed a novel sampling device which is capable of taking reliable samples, and being able to be adjusted to take a sample only after discharge stream reaches a predetermined level. The sampler is suitable for obtaining grab samples from discharge coming out of culverts, pipes, drainage ditches or other flow areas.

A liquid sampling device of the present invention comprises:

A substantially elongated tubular member having a first open end and a second open end;

A container defining a cavity for storing a predetermined quantity of liquid, said container having an open end through which said liquid is received, and a closed end, said open end of said container is coupled to said first open end of said elongated tubular member;

A pivot support member attached to said elongated tubular member which permits said substantially elongated tubular member to pivot in a vertical direction when said container has received a predetermined quantity of said liquid; and A cap attached to said second open end which permits said liquid to flow into said second open end and which closes said second open end once said container has received said predetermined amount of said liquid.

It is an object of the present invention to provide a sampling device that is reliable and inexpensive to produce.

It is an advantage of the present invention in that the disclosed invention has few moving parts, thereby increasing longevity and durability.

It is a further advantage of the present invention that it can be placed in remote areas and be left unattended, but still reliably take a sample when water discharge occurs.

It is still another advantage in that the present invention does not require a power source to operate.

It is still another advantage that the present invention can be made out of PVC, plastic and glass thereby assuring that the sample will not be contaminated by the sampler itself.

Still another advantage is that the present invention will reveal upon a casual observation whether a sample has been obtained.

Other objects and advantages will be apparent to those skilled in the art in view of the following Description.

DETAILED DESCRIPTION OF THE INVENTION

Figure 1:
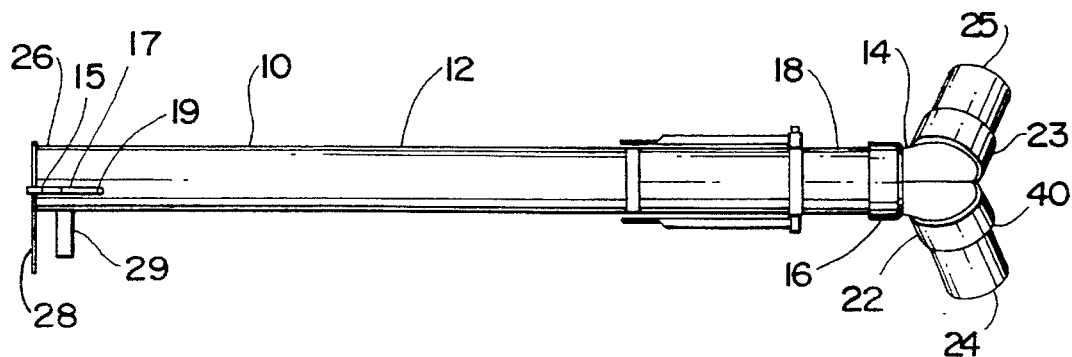
FIG. 1 shows a preferred embodiment of the present invention from a plan top view.
Figure 2:
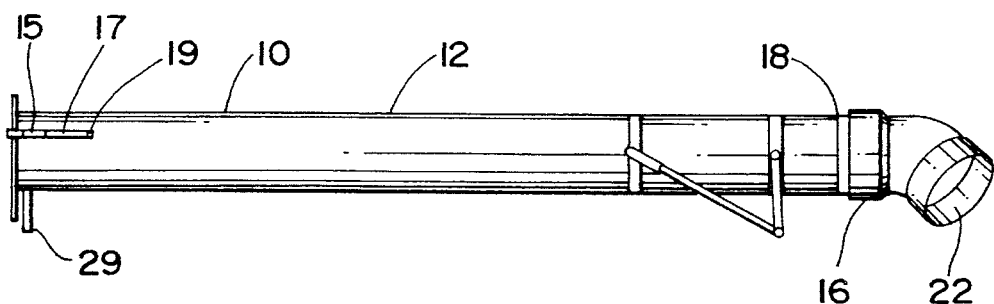
FIG. 2 shows a side view of the preferred embodiment of the present invention.

A grab sample is a single sample that will characterize a waste stream for a single point in time. The present invention will allow for inexpensive yet reliable collection of such grab samples. With reference to the accompanying drawing, FIGS. 1 and 2 shows a first embodiment of the present invention, generally designated as numeral 10. The preferred embodiment of this invention is made of 3 inch schedule 40 PVC pipe, approximately 40 inches long. Alternate materials could be used, such as thin wall stainless steel, other plated or coated metals and different plastic materials and/or the like. The substantially elongated tubular member or pipe 12 has attached to it a Y-connector or dividing means 14. The bell joint 16 of the Y-connector 14 is attached by gluing it to end 18. Orientation of the Y-connector 14 to the pipe 12 should be such that their center lines are in the same horizontal plane. Attached to the two open Y-connector openings 22 and 23 are two glass jars 24 and 25 preferably each having two quart capacity.

The glass jars or containers 24 and 25 are screwed or removably attached into the threaded Y-connector ends 22 and 23. Glass containers are preferred since glass is less likely to containment the collected sample and in many instances the collected sample will not have to be transferred to a different container for testing. However, many various other containers can be used like Teflon bags attached to the sampler with clamps thereby removing the need for the Y-connector ends 22 and 23 to be threaded.

It is envisioned that many various containers could be used instead of the glass containers so long as the container is capable of defining a cavity for storing a quantity of water or other liquid and it has an open end which can be attached to the two Y-connector open ends 22 and 23 of the Y-connector 14. The containers 24 and 25 should be, but do not have to be, depending on the samplers use, such so as to meet EPA regulations on acceptable sample containers.

In a preferred embodiment the glass containers 24 and 25 have a urethane, foam rubber jacket or other type covering to prevent the glass from breaking if it impacts the ground during use or the glass should be of the break resistant type. This all depends on if such precautions are required.

The Y-connector 14 is made by using a hand saw, and splitting (2) three-inch schedule 40 60° bend PVC and gluing them together to form a Y connection.

In the preferred embodiment, a glass containers 24 and 25 are threaded at their openings and the two open Y-connector ends 22 and 23 have an adapter 40 attached. The adapter 40 can be made from 3 inch schedule 80 PVC. The PVC pipe is cut about 2 inches long. The inside of the end that goes into the two open Y-connector ends 22 and 23 are tapered so it will match the inside of the two open Y-connector ends 22 and 23. Bevel the tapered ends to 45°. Machine out the shoulder and "O" ring grooves as shown in FIG. 7. Cut threads for the threaded container preferably a 2 quart canning jar. Providing sufficient threads to secure the container to the two open Y-connector ends 22 and 23. Preferably about four threads per inch.

Figure 4:
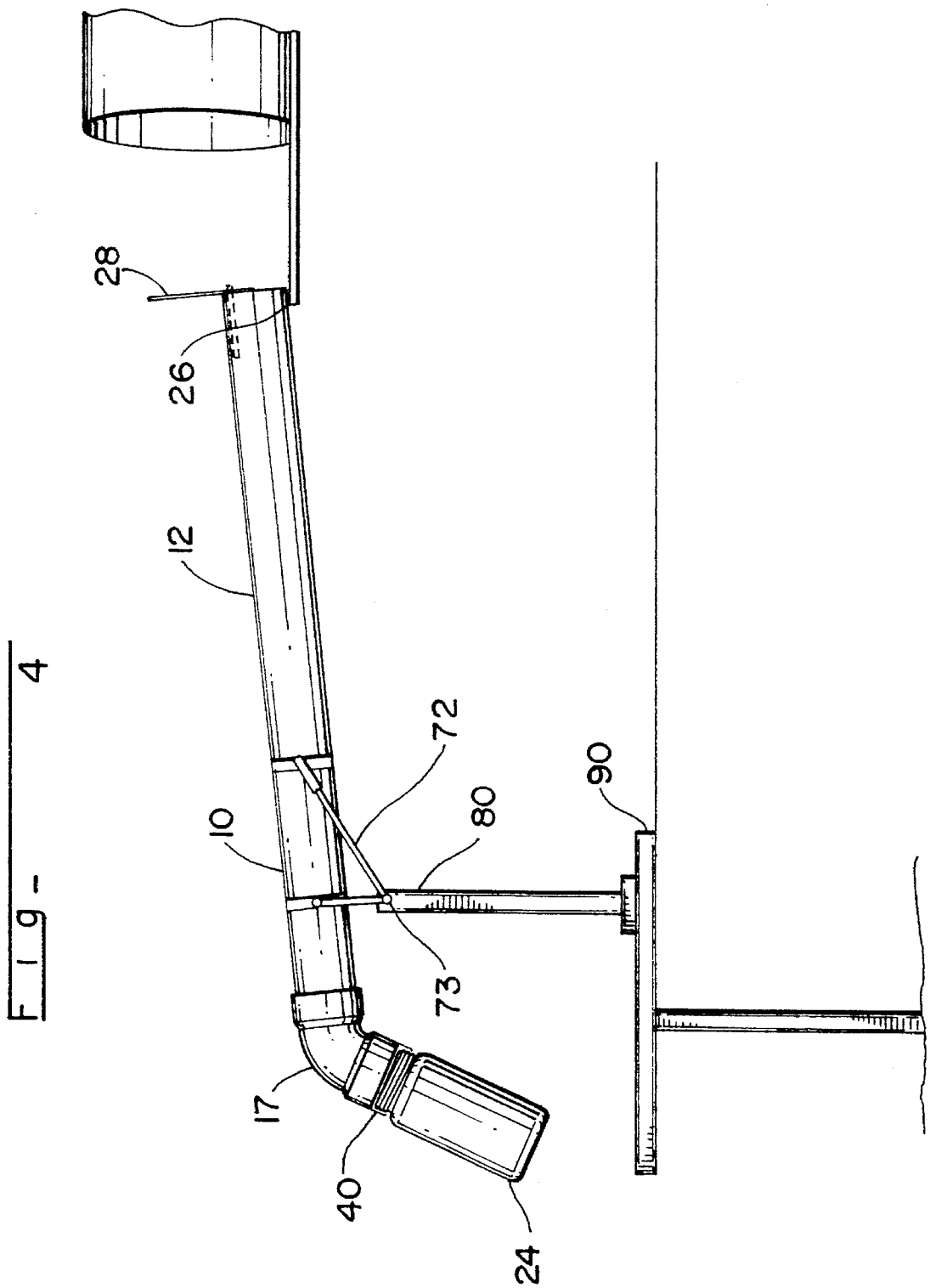
FIG. 4 is a side view of a preferred embodiment in use with a single container attached.

In the event that only 1 grab sample is required from a single discharge event the Y-connector 14 would not be needed. Accordingly, one of the containers 24 and 25 could be removably coupled to first end 18 by a threaded adapter as is described above. This would eliminate the need for the Y-connector 14. Whether it is threaded or not the a container could be removably attached to the first end 18 by a clamp or the like. The bell joint 16 of the Y-connector 14 could also be threaded so to be removably attached to the first end 18. Thereby allowing the grab sampler 10 to be easily adapted to receive either one or two samples depending on the users preference. Referring to FIG. 4 a 45° bend PVC connector can be attached to first end 18 and then the glass container 24 and 25 or the like can be attached as is described above.

Figure 3:
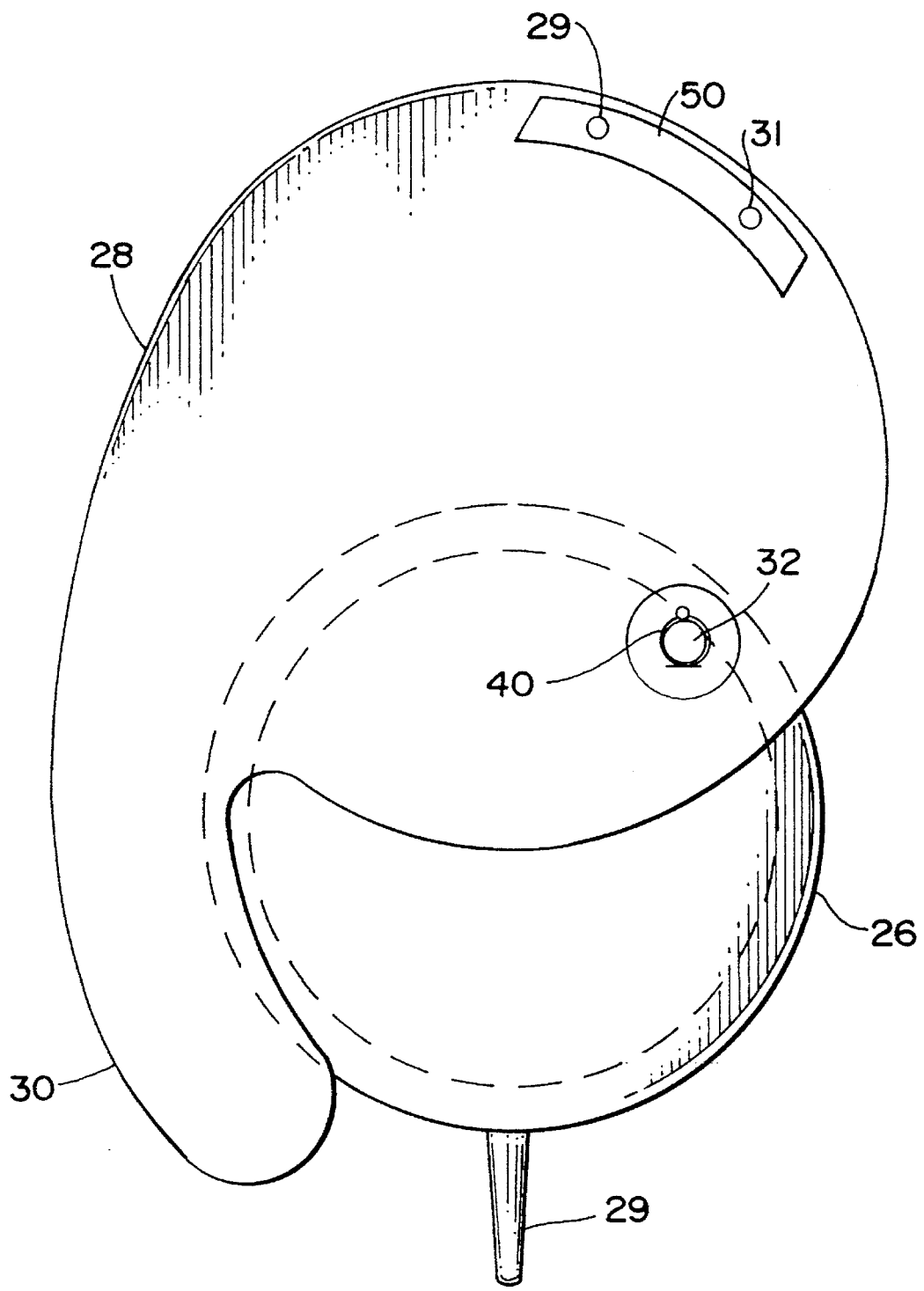
FIG. 3 shows a preferred closure means for the present invention.

Referring to FIG. 3, at the second open end 26 of pipe 12 is a closure means or flapper 28. Preferably, it has a basic diameter of 4¼ inches when the pipe 12 is 3 inches and has a handle 30 as shown. However, any diameter will be sufficient so long as it closes the second end 26 when the pipe 12 pivots upward. The gate 28 is preferably made out of "TUFFAK"®, a commercially available plastic, many various other plastics or metals would do. Preferably, the material would be durable and resist rusting. The shape and size of the handle 30 may vary so long as the closure means or cap 28 allows the second end 26 to receive liquid when the container has not yet received a predetermined amount of liquid and closes when the substantially elongated tubular member or pipe 12 pivots upward. By varying the size and shape of the handle 30 different sized openings can be created. Thereby controlling the quantity of liquid received in the sampler 10 in a given amount of time.

In a preferred embodiment, a leg or stand 29 is attached to second end 26. The stand 29 will allow the second end 26 to be elevated a predetermined distance above the supporting surface. Accordingly a sample will only be collected if the discharge stream reaches a predetermined height. It is envisioned that the handle 30 could also be modified to elevate the second end 26 above the discharge surface while still keeping the second end 26 open when no sample has been received but closed after a sample has been taken. In some instances the stand or leg 29 will not be needed thereby allowing the second open end 26 to rest directly on the surface where a discharge could occur.

The gate 28 has a hole 32 which is 17/64 inch in diameter and 1⅜ inches out from the center of gate 28 and at about a 45° angle from a horizontal line through the center of the gate 28.

The stop 50 is fabricated by cutting a piece of ¼ inch thick "TUPFAK"® or other type of plastic having an inside radius dimension of 1¾ inches and an outside radius dimension of 2⅛ inches. Cut the piece approximately 1 13/16 inches long as shown in FIG. 3. Length is not critical and may vary. Alternate materials could be used such as non-corroding metals, plated or coated metals or other suitable plastic materials. Drill holes in two places on stop 50 1 inch apart using a #43 drill to create holes 29 and 31. Tap the holes 29 and 31 using a #4-40 tap.

A pivot 40 is made by cutting a piece of ¼" stainless steel tubing 4 inches long, drill and tap in 3 holes using a #36 drill and a 6-32 tap. Drill a #36 hole ¼" from the appropriate end of the pivot. Instead of stainless, any non-corroding metal, such as brass, could be used as well as various plastics. Use of an adhesive for attachment would eliminate the necessity for the 3 each drill and tap procedure.

Drill (3) #28 holes 15,17 and 19 all the way through the body of the pipe 12 so as to allow mounting of the pivot for the flapper 28. Hole spacing could be varied so long as end result is ability to mount the pivot 40.

Using 3 each #6-32 machine screws ⅝ to ¾ inch long, attach the pivot rod 40 to the second open end 26 with the drilled end protruding so as to allow mounting of the swing gate 28. Mounting of the pivot could also be achieved by use of an adhesive to attach the pivot 40 to the sampler 10. This will eliminate the need to drill holes for the pivot.

With the gate 28 in the position as shown in FIG. 3, mark a line on the top of the gate such that a vertical line would bisect the circular part of the gate. Measure a counterclockwise 45° from the mark just made and on a 1 15/16 inch radius from the center of the cap 28, mark a first mounting hole 31 and drill with a #33 drill bit. At a 1 inch distance counterclockwise from the first hole and on the same a 1 15/16 inch radius from the center of the cap 28 drill the second hole 29 with a #33 drill bit. Attach a stop 50 by inserting the binder head stainless screw through the front of the swing gate 28 and tighten into the two drilled and tapped holes in the stop.

Mount the completed swing gate 28 on the pivot 40 by sliding the gate 28 over the pivot 40 through the 17/64 inch hole 32. Place a washer on pivot and secure with a pin or wire through the hole 32 in the pivot 40 to keep the swing gate 28 and washer in place. Then attach a washer and pin to secure pivot 40 to cap 28.

Figure 5:
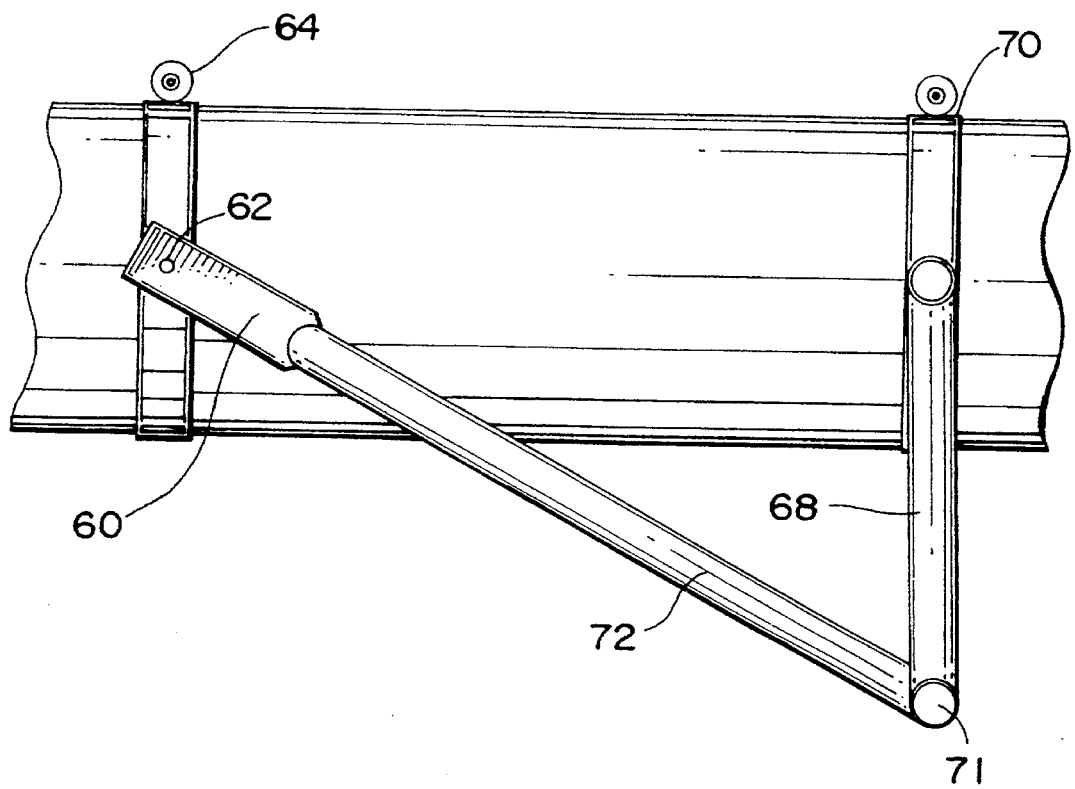
FIG. 5 is a side view of a top portion of a pivot support means of the present invention.

A pivot support member or a stand which allows pipe 12 to pivot 80 is shown in FIG. 5. It can be made in the following manner:

Cut 2 pieces of ⅜" stainless steel tubing 9.5 inches long. Flatten the end of each 60 of the above pieces on one end extending for a length of 2 inches. Using ⅛ inch drill bit, drill holes 62 ⁷⁄₁₆" from end of flattened end 60. Cut 2 pieces of ⅜ stainless steel tubing 4 inches long. Cut 2 pieces of ½ inch stainless steel tubing ⅝ inch long. Cut 1 piece of ½ inch stainless steel tubing 6⅜ inches long. Silver solder ¼ inch stainless steel tubing 1 inch long to each side of a #72 stainless steel hose clamp 64 such that they are centered on a horizontal line through the center of the hose clamp 64. Silver solder the 2 pieces of the ½ inch diameter stainless steel tubing ⅝ inch long to the 4 inch long ⅜ inch stainless by centering perpendicular at the ends. Silver solder the 4 inch long ⅜ inch diameter stainless steel tubing perpendicular to the ½ inch stainless steel tubing 71 that is 6⅜ inches long and center ⁹⁄₁₆ inch from each end.

Position and silver solder the two 9 inch long ⅜ inch diameter stainless steel tubing 68 at 60° angle as shown in FIG. 5. Rivet a #72 stainless steel hose clamp 70 by centering between the flattened ends 60 of the 9 inch long ⅜ inch diameter stainless steel tubing. Use a ⅛ inch diameter rivet with ⅛ inch to ¼ inch grip range. Slide the completed fulcrum assembly 72 over the 4 inch schedule 40 PVC pipe 12 to the appropriate location depending upon the sample volume to be collected. The purpose of the moveable fulcrum 72 is to allow selection of the volume of grab sample to be collected. The described fulcrum could be fabricated from other materials such as non-corroding metals, plated or coated metals or appropriate plastics. Adhesive could be substituted in lieu of silver soldering. Other more simple fulcrums may be used including drilling horizontal holes through the 4 inch diameter pipe 12 and inserting an appropriate size shaft. The shaft can be inserted in the proper set of holes depending on the weight and quantity of sample desired to be taken. The fulcrum 72 (and pipe 12) is field mounted by inserting an appropriate length of ⅜ inch diameter stainless steel tubing, rod or bolt through the 6⅜ inch long ½ inch diameter stainless steel tubing 71. This shaft 73 is then suspended by vertical supports 74 and 75 to provide the sampler a mounting appropriate to collect a grab sample as shown in FIG. 4.

Mounting the sampler 10, for obtaining the grab sample, requires two vertical supports 74 and 75 with holes or a top cradle suitable for supporting the horizontal sampler fulcrum. These supports 74 and 75 may vary from stainless steel angle iron to 2×4 lumber. In a preferred embodiment the vertical supports 74 and 75 are bolted to a mounting plate 90. The incline of the sampler should be at least 5° in order to insure that sample flows into the sampler. In addition, there must be sufficient clearance at the collection end of the sampler to allow the sampler to tilt up after the sample is collected.

A restraining cord, cable or chain may be used to limit the tilt of the pipe 12 after the containers have received a predetermined amount of liquid. This will prevent the containers from impacting the ground.

A screen can be inserted into or attached to the second open end 26 to prevent leaves or other materials from entering the sampler.

Water flowing into the sampler is collected in the glass container(s) 24 and/or 25 depending upon design. When the container 24 and/or 25 have collected a predetermined quantity of water, there will be sufficient weight to cause the sampler to tilt on the fulcrum, hence raising the inlet end or second open end 26 out of the sample stream and allowing the swing gate 28 to close. The swing gate 28 closes by gravity against the stop 50, hence keeping rain from diluting the sample or dust from contaminating the sample.

A casual observation will reveal whether a sample has been obtained and is ready for analysis since the inlet end 26 will be elevated after collecting the sample.

The sample collection container 24 and/or 25 may be removed from the sampler 10 by unscrewing the container 24 and/or 25.

Although only a few embodiments have been described above, those having ordinary skill in the art will readily appreciate that many modifications are possible in the preferred embodiments without materially departing from the teachings thereof. For instance, although the embodiment has been described as being formed of PVC tubing, any other kind of tubing will work. It does not have to be tubular at all but could rather be rectangular piping or any other desired shape. The support mechanism that allows for the sampler to tip up after water has been received could be made in a variety of different ways.

The closure mechanism which is attached to the second open end of the pipe need not be the flap disclosed but any other mechanical device which closes the sampler after a Predetermined quantity of water has been received and the pipe tilts upward.

Accordingly, such modifications are intended to be encompassed by the accompanying claims.

What is claimed is:

1. A grab sampler, comprising:

A substantially elongated tubular member having a first open end and a second open end;

A container defining a cavity for storing a predetermined quantity of liquid, said container having an open end through which said liquid is received, and a closed end, said open end of said container is coupled to said first open end of said elongated tubular member;

A pivot member attached to said elongated tubular member which causes said elongated tubular member to be motionless until said predetermined quantity of liquid is received into said container and which causes said substantially elongated tubular member to pivot in a vertical direction when said container has received a predetermined quantity of said liquid; and A cap attached to said second open end which permits said liquid to flow into said second open end and which closes said second open end once said container has received said predetermined amount of said liquid.

2. The grab sampler as recited in claim 1 further comprising a connector with a third open end and a forth open end with about a 60° bend between said third open end and said forth open end, third open end is attached to first open end and said container is attached to forth open end.

3. The grab sampler as recited in claim 1 further comprising a Y-connector attached to said first open end thereby allowing two containers to be coupled to said first open end.

4. The grab sampler as recited in claim 1 further comprising a leg attached to said second open end.

5. The grab sampler as recited in claim 1 wherein said cap is capable of holding second open end a predetermined distance above a liquid flow thereby preventing said liquid flow from entering into said second open end until said liquid flow reaches a predetermined height.

6. The grab sampler as recited in claim 1 wherein said container is removably coupled to said first open end.

7. A grab sampler, comprising:

A substantially elongated tubular member having a first open end and a second open end;

A dividing means attached to said first open end of said elongated member which is capable of separating said liquid into a plurality of parts;

A plurality of containers each defining a cavity for storing a quantity of liquid, said containers having an open end through which said liquid is received, and a closed end, said open end of said containers are coupled to said dividing means;

A pivot means attached to said elongated tubular member to pivot which causes said elongated tubular member to be motionless until said predetermined quantity of liquid is received into said container and which causes said elongated tubular member to pivot in a vertical direction when said containers have received a predetermined quantity of said liquid; and A cap attached to said second open end which permits said liquid to flow into said open end and which closes said second open end when said containers have received said predetermined amount of said liquid.

8. The grab sampler as recited in claim 7 wherein said dividing means is a Y-connector.

9. The grab sampler as recited in claim 7 further comprising a leg attached to said second open end.

10. The grab sampler as recited in claim 7 wherein said cap is capable of holding second open end a predetermined distance above a liquid flow thereby preventing said liquid flow from entering into said second open end until said liquid flow reaches a predetermined height.

11. The grab sampler as recited in claim 7 wherein said containers are removably coupled to said first open end.

12. A method of using a grab sample, comprising;

providing a grab sampler, comprising;

A substantially elongated tubular member having a first open end and a second open end;

A container defining a cavity for storing a predetermined quantity of liquid, said container having an open end through which said liquid is received, and a closed end, said open end of said container is coupled to said first open end of said elongated tubular member;

A pivot support member attached to said elongated tubular member which permits said substantially elongated tubular member to pivot in a vertical direction when said container has received a predetermined quantity of said liquid; and A cap attached to said second open end which permits said liquid to flow into said second open end and which closes said second open end once said container has received said predetermined amount of said liquid;

Placing said grab sampler unto an area where a discharge stream may form;

Determining whether said predetermined quantity of said liquid has been received by observing whether said elongated tubular member has tilted upward; and removing said container when said elongated tubular member is in a near vertical orientation.

13. The liquid collection device as recited in claim 12 further comprising a connector with a third open end and a forth open end with about a 60° bend between said third open end and said forth open end, third open end is attached to first open end and said container is attached to forth open end.

14. The liquid collection device as recited in claim 12 further comprising a Y-connector attached to said first open end thereby allowing two containers to be coupled to said first open end.

15. The liquid collection device as recited in claim 12 further comprising a leg attached to said second open end.

16. The liquid collection device as recited in claim 12 wherein said cap is capable of holding second open end a predetermined distance above a liquid flow thereby preventing said liquid flow from entering into said second open end until said liquid flow reaches a predetermined height.

17. A grab sampler, comprising:

A substantially elongated tubular member having a first open end and a second open end;

A container defining a cavity for storing a predetermined quantity of liquid, said container having an open end through which said liquid is received, and a closed end, said open end of said container is coupled to said first open end of said elongated tubular member;

A support means attached to said elongated tubular member which causes said elongated tubular member to be motionless until said predetermined quantity of liquid is received into said container and which causes said substantially elongated tubular member to pivot in a vertical direction when said container has received a predetermined quantity of said liquid; and A closure means attached to said second open end which permits said liquid to flow into said second open end and which closes said second open end once said container has received said predetermined amount of said liquid.

18. The grab sampler as recited in claim 17 further comprising a Y-connector attached to said first open end thereby allowing two containers to be coupled to said first open end.

19. The grab sampler as recited in claim 17 further comprising a leg attached to said second open end.

20. The grab sampler as recited in claim 17 wherein said container is removably coupled to said first open end.

* * * * *